United States Patent [19]

Casley-Smith

[11] Patent Number: 5,096,887

[45] Date of Patent: * Mar. 17, 1992

[54] TREATMENT OF HIGH PROTEIN OEDEMAS

[75] Inventor: John R. Casley-Smith, Tennyson, Australia

[73] Assignee: Lamorna Investments Proprietary Limited, Australia

[*] Notice: The portion of the term of this patent subsequent to Oct. 7, 2003 has been disclaimed.

[21] Appl. No.: 800,070

[22] PCT Filed: Mar. 1, 1985

[86] PCT No.: PCT/AU85/00036

§ 371 Date: Oct. 28, 1985

§ 102(e) Date: Oct. 28, 1985

[87] PCT Pub. No.: WO85/03865

PCT Pub. Date: Sep. 12, 1985

[30] Foreign Application Priority Data

Mar. 1, 1984 [AU] Australia .............. PG3874

[51] Int. Cl.$^5$ .............................................. A61K 31/35
[52] U.S. Cl. ........................................ 514/27; 514/457; 514/456
[58] Field of Search ............... 514/456, 457, 27

[56] References Cited

U.S. PATENT DOCUMENTS 3,155,579 11/1964 Perrault ........................... 514/456
3,567,832  3/1971 Boschetti et al. ................ 514/457
4,616,033 10/1986 Casley-Smith ................... 514/457

FOREIGN PATENT DOCUMENTS 2521584  9/1984 Australia .
2424026 11/1979 France .
 644374  7/1984 Switzerland .

OTHER PUBLICATIONS

T. J. Hardt, et al. Thesis, University of Cincinnati Medical Center (date not known).
T. Lerut, et al., *Medikon Nederland* 5, p. 1923 (1976).
Remington's Pharmaceutical Sciences; 16th Ed. (1980) pp. 1252-1253.

Primary Examiner—Frederick E. Waddell
Assistant Examiner—K. Weddington
Attorney, Agent, or Firm—Oldham & Oldham Co.

[57] ABSTRACT

A method of applying a drug selected from the benzopyrone group of drugs to an animal to treat high-protein oedemas.

4 Claims, No Drawings

TREATMENT OF HIGH PROTEIN OEDEMAS

This application is the national application corresponding to international application No. PCT/AU85/00036 filed Mar. 1, 1985 and designating the United States.

This invention relates to the treatment of high protein oedemas in animals including man, particularly the application of the benzo-pyrones to the skin and mucous membranes.

BACKGROUND OF THE INVENTION

Members of the benzo-pyrone group of drugs are known, and while the drugs have obviously been tested in a large variety of experimental conditions in laboratory animals, they have never been suggested for veterinary use.

Oedema is an abnormal accumulation of fluid in the tissue spaces or cavities of the body. There are five main factors in the formation of generalised oedema and a sixth which plays an important role in the formation of local oedema. They are:

1. Permability of the capillary wall,
2&3. Colloidal osmotic pressure of the plasma proteins in the blood and tissues,
4&5. Hydrostatic pressures in the capillaries and tissues, and
6. Lymphatic obstruction.

Thus oedema is an unusual swelling of the tissue due to an excessive amount of fluid and can be the result of various causes. Thus haematoma, or in other words a bruise, is one of the most common oedemas. The causes of oedema fall naturally into four groups corresponding to the four classes of oedema, thus 1. High-flow low-protein
2. High-flow high-protein
3. Low-flow high-protein, as well as a fourth group of causes of oedema "safety valve insufficiency" which occurs when lymphostasis is superimposed on what would normally be a high flow oedema produced either by excess blood vascular leakage, or the obstruction of a duct of an organ (kidney, pancreas, etc.) the results of which are particularly disastrous for the tissues.

High-protein oedemas are very common in all communities. It has been found that one person in three seeks medical attention every year in South Australia for a condition associated with one. The W.H.O. estimates that 250,000,000 people suffer from lymphoedema and elephantiasis, while 250,000 women in Australia suffer from lymphoedema of the arm, of varying grades of severity, after mastectomy. It is highly probably that the improvement produced by the benzo-pyrone group of drugs, in so many different diseases, is because they have high-protein oedema associated with them. This always causes reduced oxygenation and function of the tissues. If the oedema is reduced, oxygenation and function are improved. While these drugs do not affect the basic diseases, the reduction they produce in associated oedemas improve the function of the tissues and thus the normal healing processes proceed more expeditiously. Examples of this are: lymphoedema, accidental and surgical trauma, haematomas, pancreatitis, hepatitis and cirrhosis.

BRIEF DESCRIPTION OF THE INVENTION

It has been found that the group of benzo-pyrones is highly beneficial in the treatment of oedemas, particularly high protein oedemas.

Thus according to the invention there is provided a method of treating high-protein oedemas in animals including man, by the application of any member of the benzo-pyrone group of drugs to the skin or mucous membranes of the animal.

DESCRIPTION OF THE PREFERRED EMBODIMENTS

It has been shown that these drugs can effectively reduce high protein oedemas and they do this by increasing the normal proteolysis of the tissues and (to some extent) by increasing lymphatic function. They are thus effective in all diseases which have high protein oedema as part of their disorders. While they do not cure any underlying disease, the fact that they reduce the associated high protein oedema means that they relieve much pain and loss of function. In addition all oedemas cause lowered oxygenation and much harm to the tissues. The high protein ones in particular (if prolonged) cause chronic inflammation and thus their removal is of considerable benefit.

The benzo-pyrones are a group of compounds which include a number of sub-groups. They contain the flavonoids and their derivatives, coumarin and its derivatives and a variety of other groups.

It has been found that the benzo-pyrones as noted above are very effective in the treatment of high protein oedemas. It has been found that the use of the benzo-pyrone affects the oedema in four ways:

1. Excessive protein loss from the blood vessels can be reduced (under certain conditions)
2. Protein and fluid removal by the lymphatics can be increased (under certain conditions)
3. More phagocytosis of protein by cells in the tissues occurs and
4. The intracellular or extracellular, lysis of proteins by cells in the tissues are made greater.

It should be realised however that it may be rare for a benzo-pyrone to have only one action in a particular disease; similarly, it is rare for a particular disease to have only one cause or to derange only one of the body's functions. Thus for example a burn gives a high protein oedema because of the injured blood vessels, but frequently the collecting lymphatics go into spasm producing a super-imposed lymphoedema i.e. there is a 'safety-valve' insufficiency; treating a burn with a benzo-pyrone may well affect the open blood capillary endothelial junctions, interfere with the mediators of inflammation, alter the permeability of the interstitial tissue, increase the extravascular proteolysis and cause the collecting lymphatics to pump more lymph.

Benzo-pyrones, while often opening blood vascular functions, can greatly reduce blood vascular endothelial damage in certain circumstances. These include preventing the opening of the post capillary venular endothelial junctions, preventing endothelial cells leaving the vessel wall with a consequent hugh gap in its lining, and acting as vitamin-P substances when the patient is deficient in this.

It has been shown that benzo-pyrones can increase the pumping capacity of the collecting lymphatics and that they also cause an increased production of urine.

Increased phagocytosis may indeed occur, but the phagocytosed macromolecules are not retained in the tissues. In burns the removal of the protein was considerably increased by coumarin under all conditions. The removal of a non-metabolisable tracer PVP, was slowed by the coumarin in the normal and burnt legs—possibly because phagocytosis was enhanced (with the non-metabolisable PVP being retained in the phagocytes); the PVP was however more rapidly removed with coumarin in the presence of lymphodema—probably because the reduction of oedema reduced the distances it had to travel to reach blood capillaries. The important thing is that the protein removal from the limbs was much more rapid with coumarin. This shows that it is not simply phagocytosed and retained in the phagocytes in the region.

It has also been shown by exclusion that, when the benzo-pyrones reduce high protein oedemas they must increase proteolysis and secondly it was found that the ratios of radio-labelled-protein-fragments, to the labelled protein, increased greatly when treated with coumarin, thirdly that the benzo-pyrones have been shown to induce increased levels of proteases in the oedema fluid, in the whole tissues, and in the plasma and lymph, fourthly they increase proteolysis by macrophages in vitro and fifthly they lose their ability to reduce high protein oedemas when the macrophages are selectively poisoned.

Thus it can be seen that the use of benzo-pyrones, particularly coumarin is particularly effective in reducing all forms of oedema, and the dosage and treatment will vary according to the particular oedema being treated.

Thus the invention includes the use of any member of the benzo-pyrone group of drugs to treat high-protein oedemas, including:

lymphoedema and elephantiasis—including protein-losing enteropathies and other forms of lymph reflux, and transplantation oedema, also some forms of pseudotumor cerebri (lymphostatic encephalopathy)

ascites, pleural and pericardial effusions, pulmonary congestion—including asthma of allergic or traumatic origin, all forms of excessive fibrosis—including that of chronic tuberculosis, the varicose vein syndrome and chronic venous insufficiency, peripheral arterial insufficiency and the post-ischaemic syndrome, accidental and surgical trauma—including burns (heat, cold, or chemical), and cerebral and ocular oedema, acute and chronic inflammation in general—including infections, rheumatoid arthritis and all forms of auto-immune diseases, hepatitis of any cause, hepatic cirrhosis, acute and chronic pancreatitis, diabetic retinopathy and senile macular degeneration, metabolic disorders and vitamin deficiencies.

The compounds can be used to reduce hypercholesterolaemia and hyperlipidaemia and as antihelminthics and to improve postural hypotension.

It is to be noted that some benzo-pyrones kill bacteria, viruses, intestinal parasites; those which do not, at least do not worsen the conditions (e.g. during infection)—unlike the action of steroids.

Benzo-pyrones have anti-neoplastic activity and may be used to control, or destroy, neoplasms (including carcinoma and melanomas), and can be used in allergic conditions—of the skin, mucosa, and deeper organs and autoimmune diseases and demyelinating diseases—including multiple sclerosis.

The drug can be used in diabetic retinopathy, cataract, and other diabetic manefestations of increased blood vascular permeability, and to improve the functioning of the lymphatic system, to reduce the amount of dead heart muscle, and disorders of the initiation and conduction of the contraction of the heart, in myocardial infarction and other heart conditions involving oedema.

The compound can reduce fevers, pain and the desquamation of endothelial cells and in the treatment of senile blindness (diffuse maccular degeneration, including after extraction of the lens), and in the treatment of crytogenic fibrosing alveolitis.

It is to be noted that this is only a short list of the conditions associated with high-protein oedemas. Any high-protein oedema is deleterious, and that although it may not be a major part of some disease, it should always be treated if possible.

It is also used to enhance the function of macrophages, neutrophils and other cells concerned with the immune and phagocytic systems, particularly in order to increase their destruction of neoplasms, but also to increase their proteolytic and other functions, and to stabilise plasma and lysosomal membranes, to decrease erythrocyte and platelet aggregation, to normalise prostaglandin production and function, and to relax smooth muscles.

The modes of administration include: orally, rectally and vaginally; administration by injection or other methods (e.g. direct surgical placement, iontophoresis) into any part of the body including: intravenous, cutaneous, subcutaneous, intramuscular, intraperitoneal injection, application to the skin or mucous membranes, whether incorporated in a cream, powder, ointment, paste (including toothpaste), spray, lotion, or in any other manner. It may be administered either alone, or associated with other compounds with similar actions or complementary ones.

Examples included in the group of benzo-pyrones include coumarin 7 hydroxy derivatives thereof, rutin, troxerutin and diosmin.

In one example a solution of coumarin in polyethylene glycol 400 was prepared and used as a paint on the skin. Preferably a 10% by weight solution is used, but solutions of 2.5% to 20% by weight of coumarin in the polyethylene glycol 400 can be used.

In a second example 20% by weight 7 hydroxy coumarin in an inert cream, such as cetomacrosol was prepared and applied. The range of 7 hydroxy coumarin in the carrier cream can vary from 2.5% up to a maximum of 90% by weight.

However the invention does not include the use of the sodium cromoglycate, by inhalation, as this does not fall within the invention.

The claims defining the invention are as follows:

1. A method for the treatment of high protein oedema in a warm blooded animal in need of such treatment which comprises administering to the skin or mucous membrane a composition comprising a compound selected from the group consisting of coumarin, rutin and troxerutin in a pharmaceutically acceptable carrier wherein the amount of said compound is in the range of 2.5 percent to 90 percent by weight of the total composition.

2. A method according to claim 1 wherein the carrier is polyethylene glycol and the amount of said compound is in the range of 2.5 percent to 20 percent by weight of the total composition.

3. A method according to claim 1 wherein said compound is coumarin.

4. A method according to claim 1 wherein the carrier is an inert cream.

* * * * *